US006348352B1

(12) United States Patent
Shepard et al.

(10) Patent No.: US 6,348,352 B1
(45) Date of Patent: *Feb. 19, 2002

(54) METHODS FOR SELECTIVELY TRANSDUCING PATHOLOGIC MAMMALIAN CELLS USING A TUMOR SUPPRESSOR GENE

(75) Inventors: H. Michael Shepard, Rancho Santa Fe, CA (US); Nancy Kan, Dublin, OH (US)

(73) Assignee: Canji, Inc., DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/403,797

(22) PCT Filed: Sep. 17, 1993

(86) PCT No.: PCT/US93/08844

§ 371 Date: Dec. 4, 1995

§ 102(e) Date: Dec. 4, 1995

(87) PCT Pub. No.: WO94/06910

PCT Pub. Date: Mar. 31, 1994

Related U.S. Application Data

(63) Continuation-in-part of application No. 07/948,289, filed on Sep. 18, 1992, now abandoned.

(51) Int. Cl.[7] .............................................. C12N 15/88
(52) U.S. Cl. ................... 435/455; 435/320.1; 424/93.2
(58) Field of Search ........................ 514/44; 424/93.21, 424/93.6; 435/320.1, 325, 172.3, 69.1, 455; 935/34, 55, 66, 70

(56) References Cited

U.S. PATENT DOCUMENTS

| 5,087,617 A | | 2/1992 | Smith ........................... 514/44 |
| 5,219,740 A | * | 6/1993 | Miller et al. ................. 435/69.6 |
| 5,248,671 A | * | 9/1993 | Smith ........................... 514/44 |
| 5,252,479 A | | 10/1993 | Srivastava ................ 435/235.1 |
| 5,532,220 A | * | 7/1996 | Lee et al. ..................... 514/44 |
| 5,834,256 A | * | 11/1998 | Finer et al. ............... 435/91.33 |

FOREIGN PATENT DOCUMENTS

| EP | 0 475 623 A1 | 8/1991 |
| WO | WO 91/15580 | 10/1991 |
| WO | WO 93/10814 | 6/1993 |

OTHER PUBLICATIONS

Chen et al., Oncogene, 1991, 6:1799–1805.*
Friedman, Cancer Supplement, 1992, 70, 6:1810–1817.*
Huang et al., Science, 242:1563–1566, 1988.*
Mastangelo et al., Scmincus in Oncology, 23, 1: 4–21, 1996.*
Cheng et al., Cancer Res., 1992, 52, pp. 222–226 (cited in the PCT Search Report).*
Cone et al. (PNAS, vol. 81, pp. 6349–6353, 1984).*
Pei et al. (EMBASE database, AN: 92206003, Cancer Journal, 5/3, pp. 142–145, 1992, abstract).*
Culver, K.W. et al. Gene therapy for solid tumors. British Medical Bulletin 51:192–204, 1995.*
Carbone, D.P. et al. In vivo gene therapy of human lung cancer using wild–type p53 delivered by a retrovirus. J. Natl. Cancer Inst. 86:1437–1438, Oct. 4, 1994.*
Huang, H.J.S. et al. Suppression of the neoplastic phenotype by replacement of the RB gene in human cancer cells. Science 242:1563–1566, Dec. 16, 1988.*
Shaw, P. et al., "Induction of apoptosis by wild–type p53 in a human colon tumor–derived cell line," *Proc. Natl. Acad. Sci. U.S.A.* 89(10):4495–4499 (1992).
Yerly–Motta, V. et al., "Comparative preclinical study of three bone marrow purging methods using PCR evaluation of residual t(14;18) lymphona cells," *Leuk. Lymphoma* 23(3–4) :313–321 (1996).
Anderson, "Human Gene Therapy," *Science*, 256:808–813 (1992).
Baker et al., "suppression of Human Colorectal Carcinoma Cell Growth by Wild–Type p53," *Science*, 249:912–915 (1990).
Callahan, "p53 Mutations, Another Breast Cancer Prognostic Factor," *J. Natl. Canc. Inst.*, 84(11):826–827 (1992).
Casey et al., "Growth suppression of human breast cancer cells by the introduction of a wild–type p53 gene," *Oncogene*, 6:1791–1797 (1991).
Chen et al., "Genetic mechanisms of Tumor Suppression by the Human p53 Gene," *Science*, 250:1576–1580 (1990).
Chen et al., "Expression of wild–type p53 in human A673 cells suppresses tumorigenicity but not growth rate," *Oncogene*, 6:1799–1805 (1991).
Cheng et al., "Suppression of acute Lymphoblastive Leukemia by the Human Wild–Type p53 Gene," *Cancer Research*, 52(1) :222–226 (1992).
Correll et al., "Production of human glucocerebrosidase in mice after retroviral gene transfer into nutipotential hematopoietic progenitor cells," *Proc. Natl. Acad. Sci. (U.S.A.)*, 86:8912–8916 (1989).

(List continued on next page.)

*Primary Examiner*—Dave T. Nguyen
(74) *Attorney, Agent, or Firm*—Townsend and Townsend and Crew LLP (57) ABSTRACT

A method for transducing a pathologic hyperproliferative mammalian cell is provided by this invention. This method requires contacting the cell with a suitable retroviral vector containing a nucleic acid encoding a gene product having a tumor suppressive function. Also provided by this invention is a method for treating a pathology in a subject caused by the absence of, or the presence of a pathologically mutated tumor suppressor gene.

3 Claims, 4 Drawing Sheets

OTHER PUBLICATIONS

Crystal, R.G., "Transfer of Genes to Humans: Early Lessons and Obstacles to Success," *Science*, 270:404–410 (1995).

Danos et al., "Safe and efficient generatino of recombinant retroviruses with amphotropic and ecotropic host ranges," *Proc. Natl. Acad. Sci. (U.S.A.)*, 85:6460–6464 (1988).

Droz et al., "Long–term Survivors after Salvage High Dose Chemotherapy with Bone Marrow Rescue in Refractory Germ Cell Cancer," *Eur. J. Cancer*, 27(7):831–835 (1991).

Finlay et al., "The p53 Prote–Oncogene can act as a Suppressor of Transformation," *Cell*, 57:1083–1093 (1989).

Friedmann, T., *Cancer Supp*, 70(6):1810–1817 (1991).

Gaidano et al., "p53 mutations in human lymphoid malignancies Association with Burkitt lymphona and chronic lymphocytic leukemia," *Proc. Natl. Acad. Sci. (U.S.A.)*, 88:5413–5417 (1991).

Gerwin et al., "Mutant p53 can induced tumorigenic conversion of human bronchial epithlial cells and reduce their responsiveness to a negative growth factor, transforming growth factor $\beta_1$," *Proc. Natl. Acad. Sci. (U.S.A.)*, 89:2759–2763 (1992).

Guild et al., "Retroviral transfer of a murine cDNA for dultidrug resistance confers pleiotropic drug resistance to cells without prior drug selection," *Proc. Natl. Acad. Sci. (U.S.A.)*, 85:1595–1599 (1988).

Guttierrez et al., "Gene therapy for Cancer," *The Lancet*, 339:715–721 (1992).

Isaacs et al,. "Wild–Type p53 Suppresses Growth of Human prostate Cancer Cells Containing Mutant p53 Alleles," *Cancer Research*, 51:4716–4720 (1991).

Isola et al., "Association of Overexpression of Tumor Suppressor Protein p53 with Rapid Cell Proliferation and Poor Prognosis in Node–Negative breast Cancer Patients," *J. Natl. Canc. Inst.*, 84(14):1109–1114 (1992).

Johnson et al., "Expression of Wild–Type p53 is not Compatible with Continued Growth of p53–Negative Tumor Cells," *Molecular and Cellular Biology*, 11(1):1–11 (1991).

Lavigueur et al., "High incidence of Lung, Bone, and Lymphoid Tumors in Transgenic Mice Overexpressing Mutant Alleles of the p53 Oncogene," *Molecular and Cell Biology*, 9(9):3982–3991 (1989).

Ledley et al., "Clinical Considerations in the Design of Protocols for Somatic Gene Therapy," *Human Gene Therapy*, 2:77–83 (1991).

Lee, "Tumor suppressor genes: a new era for molucular genetic studies of cancer," *Breast Cancer Research and Treatment*, 19:3–13 (1991).

Levine et al., "The p53 tumour suppressor gene," *Nature*, 351:453–456 (1991).

Malkin et al., "Germ Line p53 Mutations in a Familial Syndrome of Breast Cancer, Sarcomas, and Other Neoplasms," *Science*, 250:1233–1238 (1990).

Miller et al., "Gene Transfer by Retrovirus Vectors Occurs Only in Cells That AreActively Repoicating at the Time of Infection," *Molecular and Cellular Biology*, 10(8):4239–4242 (1990).

Miller et al., "p53 Mutations in Human Lung Tumors," *Cancer Research*, 52:1695–1698 (1992).

Nigro et al., "Mutations in the p53 gene occur in diverse human tumour types," *Nature*, 342:705–708 (1989).

Rill et al., "An Approach for the Analysis of Relapse and marrow Reconstitution After Autologous Marrow Transplantation Using Retrovirus–Mediated Gene Transfer," *Blood*, 79(10):2694–2700 (1992).

Rotter et al., "p53 and Human malignancies," *Advances in Cancer Research*, 57:257–272 (1991).

Shaw et al., "Induction of apoptosis by wild–type p53 in a human colon tumor–derived cell line," *Proc. Natl. Acad. Sci. (U.S.A.)*, 89:4495–4499 (1992).

Sikora, K., "Gene therapy for cancer," *Tibtech*, 11:197–201 (1993).

Srivastava et al., "Germ–line transmission of a mutated p53 gene in a cancer–prone family with Li–Fraumeni syndrome," *Nature*, 348:747–749 (1990).

Takahashi et al., "The retinoblastoma gene functions as a frowth and tumor suppressor in human bladder carcinoma cells," *Proc. Natl. Acad. Sci. (U.S.A.)*, 88:5257–5261 (1991).

Takahashi et al., "Wild–type but not Mutant p53 Suppresses the Growth of Human Lung Cancer Cells Bearing Multiple Genetic Lesions," *Cancer Research*, 52:2340–2343 (1992).

Thor et al., "Accumulation of p53 Tumor Suppressor Gene Protein: An Independent marker of Prognosis in Breast Cancers," *J. Natl. Canc. Inst.*, 84(11):845–855 (1992).

* cited by examiner

FIG. 1A

5 X 10⁶ CELLS PER INJECTION

FIG. 1B

1 X 10⁷ CELLS PER INJECTION

METHODS FOR SELECTIVELY TRANSDUCING PATHOLOGIC MAMMALIAN CELLS USING A TUMOR SUPPRESSOR GENE

This application is a continuation-in-part of U.S. Ser. No. 07/948,289, filed Sep. 18, 1992, now abandoned.

FIELD OF THE INVENTION

The present invention generally relates to a method for selectively transducing pathologic hyperproliferative mammalian cells in a heterogeneous cell preparation comprising retroviral-mediated transduction of the pathologic cell with a nucleic acid encoding a gene product having tumor suppressive function.

Throughout this application various publications are referenced within parentheses. The disclosures of these publications in their entireties are hereby incorporated by reference in this application in order to more fully describe the state of the art to which this invention pertains.

BACKGROUND OF THE INVENTION

The human p53 gene encodes a 53 kilodalton nuclear phosphoprotein (Lane, D. P., et al., *Genes and Dev.*, 4:1–8 (1990); Lee, Y-HP, *Breast Cancer Res.and Trmt*, 19:3–13 (1991); Rotter, V., et al., *Adv. Can. Res.*, 57:257–72 (1991)). The p53 protein was first identified as a cellular protein in SV40-transformed cells that was tightly bound to the SV40 T antigen (Lane, D. P., et al. *Nature*, 278:261–3 (1979)). The wild type p53 gene has the characteristics of a tumor suppressor gene. It is similar to the prototype of tumor suppressor genes, the retinoblastoma gene (RB), in that loss of heterozygosity of the p53 or RB genes characterizes the phenotype of many types of tumor cells (Hollstein, M. et al., *Science*, 253:49–51 (1991); Levine, A. J., et al., *Biochimica et Biophysica Acta*, 1032:119–36 (1990); Levine, A. J., et al., *Nature* 351:453–6 (1991); Weinberg, R. A. *Science*, 254:1138–46 (1991)). In human malignancies associated with p53 alterations, this loss of heterozygosity usually results from the loss of one allele (allelic deletion), while the other allele suffers one or more somatic mutations. Unlike RB, however, certain mutations in the p53 gene are capable of immortalizing rodent cells and enhancing the tumorigenicity of established cell lines (Jenkins, J. R., et al., *Nature*, 312:651–4 (1984)). Mutant but not wild type p53 can cooperate with the activated ras oncogene in transforming primary rat embryo fibroblasts (Eliyahu, D., et al., *Nature*, 312(13):646–9 (1984); Parada, L. F., et al., *Nature*, 312:649–51 (1984)). Other events related to tumor progression also appear to be associated with the expression of mutant p53. Among these is differential modulation of the multiple drug resistance gene (MDR1) by wild type as compared to altered p53. In this case, mutant p53 specifically stimulates the MDR1 promoter, while wild type p53 exerts repression (Chin, K-V., et al., *Science*, 255:459–62 (1992)). Another possible way in which mutant p53 could promote tumorigenesis is by reducing tumor cell responsiveness to transforming growth factor-β, a negative regulator of cell proliferation (Gerwin, B. I., et al., *PNAS USA*, 89:2759–63 (1992)).

In addition to the in vitro data described above two animal models have been described that implicate p53 in tumor formation. Transgenic mice expressing a mutant p53 gene display a high incidence of lung, bone and lymphoid tumors (Lavigueur, A., et al. *Mol. Cell. Biol.*, 9(9):3982–91 (1989)). In addition, p53-null mice (Donehower, L. A., et al., *Nature*, 356(19):215–21 (1992)) show an increased risk of spontaneous neoplasms, the most frequently observed being malignant lymphoma.

Other data which support the conclusion that mutant p53 plays an important role in tumorigenesis include re-introduction of the wild type p53 gene into human tumor cell lines which lack p53 expression. In this case, wild type p53 can reverse the malignant phenotype as measured by colony formation in soft agar and tumor formation in nude mice (Chen, P. L., et al., *Science*, 250:1576–80 (1990); Cheng, J., et al., *Can. Res.*, 52:222–6 (1992); Baker, S. J., et al., *Science*, 249:912–15 (1990); Isaacs, W. B., et al., *Can. Res.*, 51:4716–20 (1991); Casey, G., et al., *Oncogene*, 6(10):1791–7 (1991); Shaw, P., et al., *PNAS USA*, 89:4495–99 (1992); Takahashi, T., et al., *Can. Res.*, 52:2340–3 (1992)). Tumor cell types which have shown conversion of a non-malignant phenotype as a result of the introduction of wild type p53 expression include prostate (Isaacs, W. B., et al., supra), breast (Casey, G. et al. supra), colon (Baker, S J., et al., supra; Shaw, P. et al., supra) lung (Takahashi, T. et al., supra), and lymphoblastic leukemia (Cheng, J. et al., supra). Other data suggest that introduction of wild type p53 into tumor cells which have lost endogenous p53 expression appears to be cytotoxic (Johnson, P. et al., *Mol. Cell. Biol.*, 11(1):1–11 (1991)). In some cases the re-introduction of wild type p53 may result in programmed cell death, or apoptosis (Yonish-Rouach, E. et al., *Nature*, 352:345–7 (1991)). The work described above indicates strongly that alteration of the wild type p53 gene has a role in multiple aspects of tumorigenesis and that reintroduction of the wild type p53 coding sequence can have a negative regulatory function or cytotoxic effect on malignant cells.

Clinical data suggest that inactivating mutations in the p53 gene are among the most common types of mutations associated with human malignancy (Rotter, V. et al. supra; Nigro, J. M. et al., *Nature*, 342:705–8 (1989); Gaidano, G. et al., *PNAS USA*, 88:5413–7 (1991); Cheng, J. et al., *Mol. Cell. Biol.*, 10(10):5502–09 (1990)). A classical example is the Li-Fraumeni syndrome, a familial syndrome of several neoplasms, including breast cancer, sarcomas and others. Specific mutations in the p53 gene are found in affected members of the family and appear to be associated with the predisposition to develop early cancers (Malkin, D. et al., *Science*, 250:1233 (1990); Srivastava, S. et al., *Nature*, 348:747 (1990)). Several laboratories have reported that alterations in the p53 gene accompany the evolution of human CML (chronic myelogenous leukemia) to blast crisis (acute phase) (Ahuja, H. et al., *J.Clin.Invest.*, 87:2042–7 (1991); Foti, A. et al., *Blood*, 77(11):2441–4 (1991); Feinstein, E. et al., *PNAS USA*, 88:6293–7 (1991)). In one CML patient who reverted briefly from the acute phase to a second chronic phase, the inactivating point mutation in p53 which appeared concomitantly with the acute phase disappeared and the wild type sequence re-emerged (Foti, A. et al., supra). These data indicate that alterations which inactivate the tumor suppressive activity of p53 may represent pivotal events in the progression from the chronic to the acute phase of human CML. Other clinical data also suggest an important role for p53 mutations in disease progression. These include a number of hematologic neoplasms as well as solid tumors (Rotter, V. et al. supra; Ahuja, H. et al., *J.Clin.Invest.*, supra; Ahuja, H. et al., *PNAS USA*, 86:6783–6787 (1989); Mori, N. et al., *Br. J. of Haem.*, 81:235–240 (1992); Porter, P. L. et al., *Am.J.Path.*, 140(1):145–53 1992)). Recent reports show a dramatic association between altered p53 and shortened survival in breast cancer (Thor, A. D. et al., *J. Natl.Can. Inst.*, 84(11):845–55 (1992);

Isola, J. et al., *J.Natl. Can. Inst.*,84(14):1109–14 (1992); Callahan, R. *J.Natl. Can.Inst.*, 84:826–7 (1992)).

SUMMARY OF THE INVENTION

The present invention generally relates to a method for selectively transducing pathologic hyperproliferative mammalian cells comprising retroviral-mediated transduction of pathologic cells with a nucleic acid encoding a gene product having tumor suppressive function. The methodology provided involves the introduction of a stably expressed tumor suppressor gene into a heterogeneous cell preparation (containing both normal and pathologic hyperproliferative cells) and, under suitable conditions, selectively transducing phenotypically pathologic hyperproliferative cells, suppressing the pathologic phenotype and reinfusing the treated cell preparation into the patient. Also provided by this invention is a method for treating a pathology in a subject caused by the absence of, or the presence of a pathologically mutated tumor suppressor gene.

BRIEF DESCRIPTION OF THE FIGURES

FIG. 1 shows the tumorigenicity of antibiotics-selected K562 cells in nude mice. K562 cells were infected with the p53-RV or NCV and selected in hygromycin as described in the legend to Table 3. (A) $5 \times 10^6$ K562/p53 or K562/NCV (B) $1 \times 10^7$ K562/p53 or K562/NCV were injected subcutaneously into opposite flanks of athymic Balb/c nu/nu mice. The mice were purchased from Simonsen Laboratories, Inc. (Gilroy, Calif.) and maintained in a pathogen-free environment. Once tumors were formed, they were measured weekly until the experiments were terminated.

DETAILED DESCRIPTION OF THE INVENTION

There are approximately 5,000 bone marrow transplantations (BMT) each year (*The BBI Newsletter*, 156 (1991)). Most of these are performed on leukemia and lymphoma patients. A growing number of BMT are being done to support more intensive therapeutic approaches to breast and lung cancers, as well as for other indications (Droz, J. P. *Eur. J. Can.*, 27:831–35 (1991); Menichella, G. *Br.J. Haem.*, 79:444–50 (1991); Osbourne, C. K. *Breast Can. Res. Trtmt.*, 20:511–14 (1991)). Approximately 30% of these patients are candidates for tumor suppressive gene therapy. This number derives from the observation that about 30% of cancer patients either do not express the tumor suppressor gene or express an inactivated form of the tumor suppressor protein (Hollstein, M. et al., supra). The preferred embodiments detailed below support the efficaciousness of a retrovirus encoding the human wild type tumor suppressor gene, p53-RV, in reversing the malignant phenotype of several leukemia and lymphoma cell lines as measured by abrogation or substantial inhibition of colony formation in soft agar assays, and as judged by reversing/inhibiting the ability of tumor cells to grow in nude mice following introduction of the wild type p53 gene.

For the K562 tumor cell line, which is derived from a chronic myelogenous leukemia patient in blast crisis (Andersson, L. C. et al., *Int. J. Can.*, 23:143–7 (1979)) for two human small-cell lung carcinoma cell lines (H69 and H128) (Gazdar, A. F. et al,. *Can. Res.*, 40(10):3502–7 (1980)), and for one transitional cell (bladder) carcinoma cell line (HTB9) (Takahashi, R. et al., *PNAS USA*, 88:5257–61 (1991)) tumor suppression by p53 can be accomplished with a protocol involving short-term infections with the p53-RV. This protocol is completely consistent with current clinical methodology used in the preparation of bone marrow or peripheral blood hematopoietic cells for autologous bone marrow transplantation (ABMT) (Deisseroth, A. B. et al., *Human Gene Therapy*, 2:359–376 (1991)).

The present invention generally relates to an improved method of gene therapy for "negative purging" of pathologic hyperproliferative cells that contaminate preparations of autologous hematopoietic cells used for bone marrow reconstitution. As used herein, the term "hyperproliferative cells" includes but is not limited to cells having the capacity for autonomous growth, i.e., existing and reproducing independently of normal regulatory mechanisms. Hyperproliferative diseases may be categorized as pathologic, i.e., deviating from normal cells, characterizing or constituting disease, or may be categorized as non-pathologic, i.e., deviation from normal but not associated with a disease state. Pathologic hyperproliferative cells are characteristic of the following disease states, thyroid hyperplasia—Grave's Disease, psoriasis, benign prostatic hypertrophy, Li-Fraumeni syndrome including breast cancer, sarcomas and other neoplasms, bladder cancer, colon cancer, lung cancer, various leukemias and lymphomas. Examples of non-pathologic hyperproliferative cells are found, for instance, in mammary ductal epithelial cells during development of lactation and also in cells associated with wound repair. Pathologic hyperproliferative cells characteristically exhibit loss of contact inhibition and a decline in their ability to selectively adhere which implies a change in the surface properties of the cell and a further breakdown in intercellular communication. These changes include stimulation to divide and the ability to secrete proteolytic enzymes. The present invention will allow for high dose chemotherapy and/or radiation therapy, followed by autologous bone marrow reconstitution with hematopoietic cell preparations in which phenotypically pathologic cells have been reconstituted with a normal tumor suppressor gene. Application of the present invention will result in diminished patient relapses which occur as a result of reinfusion of pathologic hyperproliferative cells contaminating autologous hematopoietic cell preparations.

More specifically, the present invention relates to a method for depleting a suitable sample of pathologic mammalian hyperproliferative cells contaminating hematopoietic precursors during bone marrow reconstitution via the introduction of a stably-expressed wild type tumor suppressor gene into the cell preparation (whether derived from autologous peripheral blood or bone marrow). As used herein, a "suitable sample" is defined as a heterogeneous cell preparation obtained from a patient, e.g., a mixed population of cells containing both phenotypically normal and pathogenic cells. An example of a wild type tumor suppressor gene is the p53 gene, the coding sequence of which has been described by Chen et al. supra and the amino acid sequence is shown in Table 1. (SEQ ID NOS: 1–2)

USA, 86:8912–52 (1989); Culver, K. et al., PNAS USA, 88:3155 (1991); Rill, D. R. et al.,Blood, 79(10):2694–700 (1992)). Clinical investigations have shown that there are few or no adverse effects associated with the viral vectors (43: Anderson, Science, 256:808–13 (1992)). However, these methods have been limited to transfers of "gene markers" such as the neomycin gene that merely function as "tracking agents" for marking malignant cells before, and locating malignant cells after, reinfusion of bone marrow, however, the transduction of gene markers confers little clinical benefit to the affected patient who does not receive protection against subsequent relapse (Rill, D. R. et al. Blood, supra). The subject invention eliminates the necessity of the time consuming procedure of transducing cell samples with a selectable marker gene, such as neomycin, to identify pathologic cells to facilitate subsequent attempts to remove those cells before reinfusion into the patient.

TABLE 1

```
                                                        MEEPQ   50
SDPSV EPPLS QETFS DLWKL LPENN VLSPL PSQAM DDLML SPDDI EQWFT  100

EDPGP DEAPR MPEAA PPVAP APAAP TPAAP APAPS WPLSS SVPSQ KTYQG  150

SYGFR LGFLH SGTAK SVTCT YSPAL NKMFC QLAKT CPVQL WVDST PPPGT  200

RVRAM AIYKQ SQHMT EVVRR CPHHE RCSDS DGLAP PQHLI RVEGN LRVEY  250

LDDRN TFRHS VVVPY EPPEV GSDCT TIHYN YMCNS SCMGG MNRRP ILTII  300

TLEDS SGNLL GRNSF EVRVC ACPGR DRRTE EENLR KKGEP HHELP PGSTK  350

RALPN NTSSS PQPKK KPLDG EYFTL QIRGR ERFEM FRELN EALEL KDAQA  400

GKEPG GSRAH SSHLK SKKGQ STSRH KKLMF KTEGP DSD*
```

* = Stop codon

The preferred delivery system for the wild type tumor suppressor gene is a replication-incompetent retroviral vector. As used herein, the term "retroviral" includes, but is not limited to, a vector or delivery vehicle having the ability to selectively target and introduce the coding sequence into dividing cells. As used herein, the terms "replication-incompetent" is defined as the inability to produce viral proteins, precluding spread of the vector in the infected host cell. An example of such vector is p53-RV, which has been described in detail by Chen et al. supra and is shown in Table 2.

TABLE 2

General Schematic of p53-Retrovirus
(p53-RV)

Amphotropic Retrovirus

Propagated in PA12 (3T3-derived) cells

Titer ~1–3×10⁶ Hygromycin Resistant CFU/ml

Another example of a replication-incompetent retroviral vector is LNL6 (Miller, A. D. et al., BioTechniques 7:980–990 (1989)). The methodology of using replication-incompetent retroviruses for retroviral-mediated gene transfer of gene markers is well established (Correll, P. H. et al., PNAS USA, 86:8912 (1989); Bordignon, C. et al., PNAS Other vectors are suitable for use in this invention and will be selected for efficient delivery of the nucleic acid encoding the tumor suppressor gene. The nucleic acid can be DNA, cDNA or RNA.

The subject invention provides a "shotgun" procedure whereby the cell sample is contacted with a retroviral vector in the absence of selective medium that does not necessarily contain a selectable marker gene, but notwithstanding, possesses the ability to simultaneously selectively target and transduce only the pathologic cell population in the heterogeneous cell preparation. Other methods of efficient delivery or insertion of a gene of interest into a cell are well known to those of skill in the art and comprise various molecular cloning techniques. As used herein, the terms "insertion or delivery" encompass methods of introducing an exogenous nucleic acid molecule into a cell.

A variety of techniques have been employed in an attempt to deplete marrow of pathologic hyperproliferative cells before reinfusion, utilizing "purging" methods, e.g., monoclonal antibodies or chemotoxins (Kaizer H. et al., Blood, 65:1504 (1985); Gorin, N. C. et al., Blood, 67:1367 (1986); De Fabritiis, P. et al., Bone Marrow Transplant, 4:669 (1989)). As used herein, the term "pathologic" includes abnormalities and malignancies induced by mutations and failures in the genetic regulatory mechanisms that govern normal differentiation that are not the result of gene loss or mutation. These techniques, however, have not resulted in reduced relapse rates, and have consistently resulted in damaging normal marrow progenitor cells (Kaizer H. et al., supra; Gorin, N. C. et al., supra; De Fabritiis, P. et al., supra). The present invention addresses the aforementioned inadequacies and confers related advantages as well. These advantages include: (a) the use of a recombinant retroviral vector that does not require a selectable marker gene in combination with a short-term infection in the absence of selective medium eliminating the time consuming procedure traditionally employed to "selectively mark" the target cells before any "purging" of such cells is attempted, thereby dramatically reducing the time traditionally required for preparing hematopoietic cells for transplants; and (b) the retroviral mediated delivery methodology of the subject invention offers selective targeting of pathologic hyperproliferative cells in resting cultures of hematopoietic cells as a result of the higher infection frequency by the retroviral delivery system into actively dividing tumor cells (Miller et al., *Mol. Cell. Biol.*, 10(8):4239–42 (1990)).

The ex-vivo introduction of a wild type tumor suppressor gene, via an efficient delivery system into pathologic hyperproliferative cells contaminating peripheral blood- or marrow-derived autologous hematopoietic cells will facilitate suppression of the hyperproliferative phenotype, by inducing transformation of the cell to a mature or benign phenotype or, alternatively, by inducing apoptosis or programmed cell death, thereby allowing patients receiving ABMT to have a longer, relapse-free survival. As used herein, the term "mature or benign cell" refers to the phenotypic characteristic of inability to invade locally or metastasize.

This invention further provides a method for transducing a pathologic hyperproliferative mammalian cell by contacting the cell with a suitable retroviral vector containing a nucleic acid encoding a gene product having a tumor suppressive function, under suitable conditions such that the cell is transduced. In one embodiment, the gene product is expressed by a tumor suppressor gene and the tumor suppressor gene can be, but is not limited to wild type p53 gene, retinoblastoma gene RB, Wilm's tumor gene WT1 or colon carcinoma gene DCC. Additionally, the nucleic acid is DNA, cDNA or RNA.

The suitable conditions for contacting can be by infecting the sample cells in the absence of selective medium. "Suitable retroviral vector" has been defined above. This method is particularly useful when the pathological cells being contacted are prostate cells, psoriatic cells, thyroid cells, breast cells, colon cells, lung cells, sarcoma cells, leukemic cells or lymphoma cells.

The suitable time period for contacting can be less than about ten hours, or more specifically, about four hours. Transduction can be known to be complete, for example, when the hyperproliferative phenotype is characterized by the transduced cell expressing a mature or benign phenotype or by apoptosis or death of the transduced cell. This method has been shown to reduce tumor formation or tumorigenicity in a subject.

This method can be practiced ex vivo or in vivo. The practice of the ex vivo method is described above. When the method is practiced in vivo, the retroviral vector can be added to a pharmaceutically acceptable carrier and systemically administered to the subject. In one embodiment, the subject is a mammal, such as a human patient. Acceptable "pharmaceutical carriers" are well known to those of skill in the art and can include, but not be limited to any of the standard pharmaceutical carriers, such as phosphate buffered saline, water and emulsions, such as oil/water emulsions and various types of wetting agents.

As used herein, the term "administering" for in vivo purposes means providing the subject with an effective amount of the vector, effective to inhibit hyperproliferation of the target cell. Methods of administering pharmaceutical compositions are well known to those of skill in the art and include, but are not limited to, microinjection, intravenous or parenteral administration. Administration can be effected continuously or intermittently throughout the course of treatment. Methods of determining the most effective means and dosage of administration are well known to those of skill in the art and will vary with the vector used for therapy, the purpose of the therapy, the cell or tumor being treated, and the subject being treated.

The following examples are intended to illustrate, not limit this invention.

EXAMPLE I

Introduction of the p53-RV into Leukemia or Lymphoma-Derived Cell Lines Suppresses the Malignant Phenotype as Measured by Colony Formation in Soft Agar The retroviral vector carrying the human wild type p53-cDNA has been described (Chen et al. supra). p53-RV, an amphotropic retrovirus, is capable of infecting a wild range of human cell types (see below). This feature provides an advantage for ex vivo therapy of human leukemias, because the viral vector can deliver the wild type p53-cDNA into a number of different leukemic or other cell types, including tumor cells from solid tumors which may metastasize to marrow. The results of soft-agar assays using three leukemia or lymphoma cell lines following viral infection and antibiotic selection are shown in Table 3. In all three cases (HL-60, acute promyelocytic leukemia, p53-negative; Hut 78, acute T cell lymphoma, p53-negative; and Molt 3, acute lymphoblastic leukemia, mutant p53-positive) the introduction of wild type p53 by the p53-RV resulted in either a reduction or elimination of colony formation in soft agar.

TABLE 3

| Cell Line | No. of Cells Seeded | Plating Efficiency |
| --- | --- | --- |
| HL-60 | $5 \times 10^5$ | TMTC |
| HL-60/T* | $5 \times 10^5$ | 4.7% |
| HL-60 | $10^5$ | 43% |
| HL-60/T* | $10^5$ | 0% |
| HL-60 | $5 \times 10^4$ | 55% |
| HL-60/T* | $5 \times 10^4$ | 0% |
| Hut 78 | $10^5$ | 9.4% |
| Hut 78/I# | $10^5$ | 0.39% |
| Hut 78 | $5 \times 10^4$ | 9.2% |
| Hut 78/I# | $5 \times 10^4$ | 0% |
| Molt 3 | $10^5$ | 11.7% |
| Molt 3/I# | $10^5$ | 1.5% |

*Transfected
Infected

The human leukemic cell lines, HL-60, Hut 78 and Molt 3, were obtained from American Type Culture Collection (ATCC). The cell lines Hut 78 and Molt 3 were infected with the p53-RV and the HL-60 cell line was transfected with p53-RV DNA. The p53-RV containing the wild type p53 cDNA isolated from human fetal brain and Moloney murine leukemia viral vector has been described by Chen et al., supra. This virus also carries the hygromycin resistant gene whose expression is driven by the Rous sarcoma virus (RSV) promoter sequence. The murine NIH3T3-derived packaging cell line, PA12 (Chen et al., supra), produces the p53-RV with titers ranging from $1 \times 10^5$ to $1 \times 10^6$ virus per ml.

Viral infections were carried out overnight in the presence of 4 µg/ml polybrene. At the end of infections, 4 ml of fresh media were added to 2 ml of each infection mixture. The cells were selected in the presence of 400 μg/ml hygromycin 2 days after infection.

Infected cells grew to confluency in 2–3 weeks following hygromycin selection. For the soft-agar assay, the cells were seeded in 6-well plates at the cell densities ranging from 103 to 105 in 0.33% agar as described (Chen et al., supra). Colonies consisting of more than 50 cells were scored 2 weeks later.

EXAMPLE II

Suppression of Colony Formation in Soft Agar by K562 (Human Chronic Myelogenous Leukemia) Cells Following a Short-term Infection with p53-RV Mammalian cells infected with a retroviral vector carrying an antibiotic marker are usually pre-selected in vitro before testing for tumorigenicity in soft agar or in nude mice (Chen et al., supra, Cheng et al., supra). Because this process takes about three weeks, it would be cumbersome and expensive to pursue in the clinic. To mimic more closely the clinical situation in which tumor suppressor gene therapy may be applied during bone marrow purging, K562 cells were infected with p53-RV for four hours in vitro, then immediately tested their ability to form colonies in soft agar without any selection. A retroviral vector identical to p53-RV, but with the p53 coding sequence deleted, was used as a control (see Table 4). This vector is designated NCV (Negative Control Virus). As shown in Table 4, p53-RV decreased colony formation by infected K562 cells in a dose-dependent manner. At a multiplicity of infection, (MOI) of 1, the plating efficiencies of the p53 and NCV-infected cells were similar. However, at MOI of 3 and 10, there was a marked decrease in the plating efficiency of the p53-RV infected cells. The plating efficiencies of the NCV-infected K562 cells were similar at all three multiplicities of infection. The latter result suggests that the does-dependent reduction in tumor cell colony formation observed with increasing doses of p53-RV was due to introduction of the wild type p53. Furthermore, the result with NCV indicates that there is little non-specific toxicity associated with the retroviral infection up to MOI of 10, as measured by this assay.

TABLE 4

| Virus Infection | No. of Cells Seeded | M.O.I. | Plating Efficiency (Colony No.) |
|---|---|---|---|
| p53-RV | $10^4$ | 1 | 3.10% (310) |
|  |  | 3 | 0.52% (52) |
|  |  | 10 | 0% (0) |
| Control RV | $10^4$ | 1 | 4.30% (430) |
|  |  | 3 | 5.30% (530) |
|  |  | 10 | 3.40% (340) |
| p53-RV | $5 \times 10^3$ | 1 | 4.40% (220) |
|  |  | 3 | 1.80% (90) |
|  |  | 10 | 0.25% (13) |
| Control RV | $5 \times 10^3$ | 1 | 4.70% (235) |
|  |  | 3 | 4.10% (205) |
|  |  | 10 | 6.50% (325) |

Human chronic myelogenous leukemia (CML)-derived cell line, K562, was obtained from ATCC, Accession No. CCL243. To perform the short-term infections, K562 cells were infected with the p53-RV or NCV for 4 hours as described in Example I. Multiplicity of infection (MOI) was determined from the titer of the viral stocks and K562 cell number. At the end of infection, the viral supernatant was removed by pelleting the cells, and the concentrated cells were used immediately in the soft-agar assay as described in Example I.

To construct NCV, the plasmid containing the p53 viral genome was partially digested with BamHI, ligated, and used to transform *E. coli*. The plasmid with the deleted p53 gene was then selected by restriction enzyme analysis of mini-lysate DNA. This DNA was used to transfect/infect PsiCRIP packaging cell line as described (Danos, O. et al., *PNAS USA*, 85:6460–64 (1988)). The viral stock, termed negative control virus (NCV), was produced in PsiCRIP packaging cell line (56: Danos et al., supra) with a titer of about $2 \times 10^5$ virus per ml.

EXAMPLE III

Figure 1A:
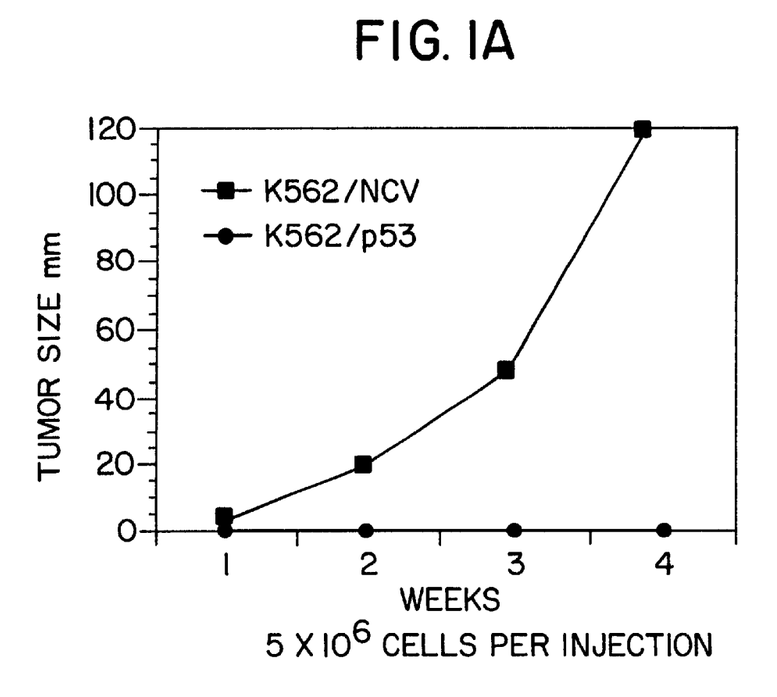
Figure 1B:
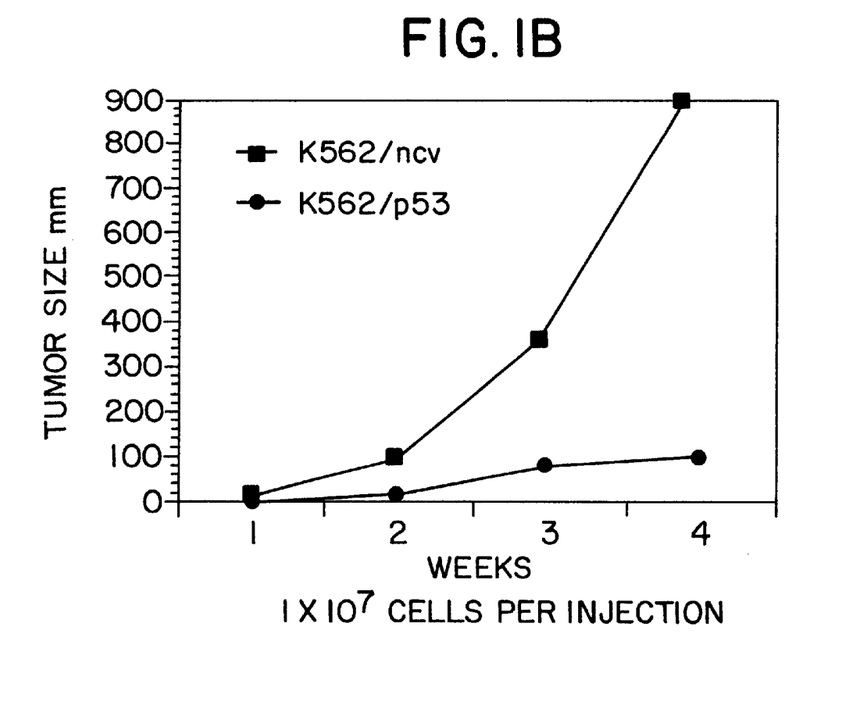

Tumorigenicity of K562 Chronic Myelogenous Leukemia Cells Following Infection by p53-RV and Selection for Hygromycin-resistant Cells To further broaden the efficacy experiments in relevant human tumor cell lines, K562 leukemic cells were infected with the p53-RV and hygromycin-resistant colonies (K562/p53) were tested for tumorigenicity in nude mice. When $5 \times 10^6$ K562/p53 cells were injected subcutaneously into nude mice, no tumor formation was observed. In contrast, a comparable number of K562/NCV cells produced tumors in all five animals tested (FIG. 1A). When $1 \times 10^7$ tumor cells were injected, the p53-RV infected cells produced visible tumors, although much smaller than those induced by the NCV-infected cells (FIG. 1B). It is likely that the lesions which formed on the flank of the animal injected with K562/p53 were induced by those cells which had lost expression of the wild type p53 gene (Johnson et al., supra). This conclusion is supported by the inability to detect p53 protein or transcripts in hygromycin selected clones after only a few passages in vitro (data not shown).

EXAMPLE IV

Figure 2:
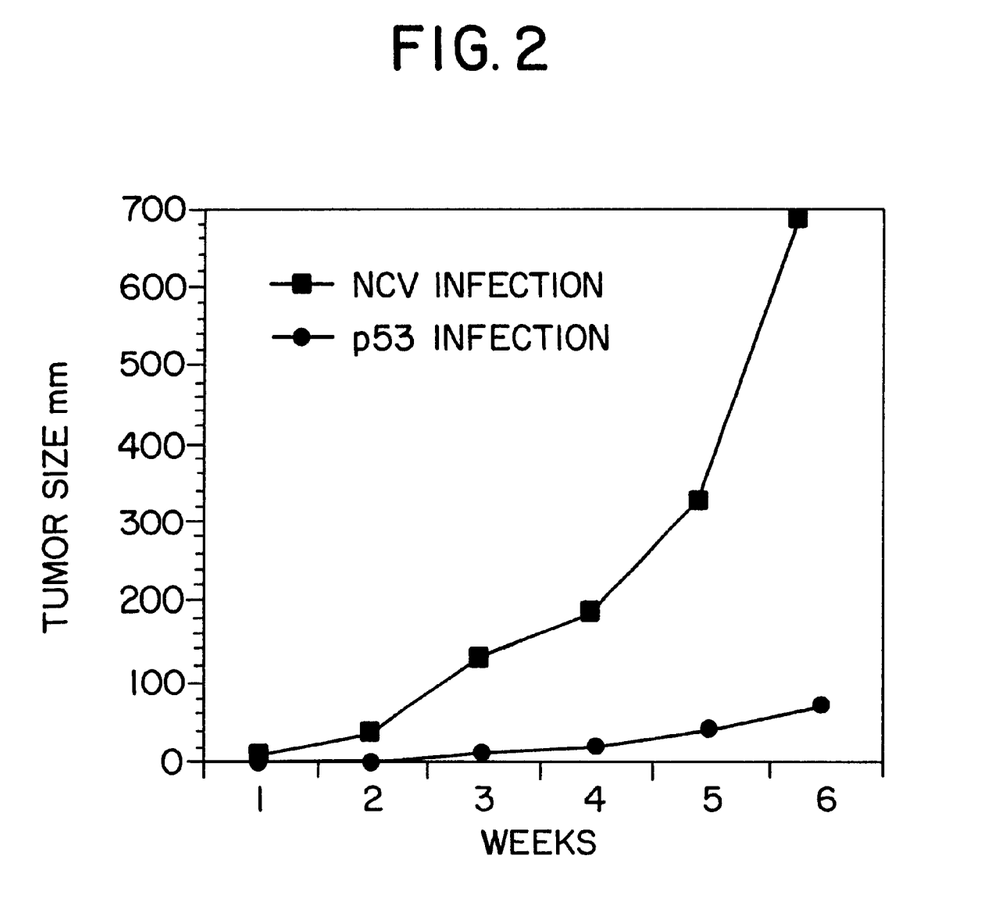
FIG. 2 shows delayed tumor formation in nude mice induced by K562 cells following a short-term infection with the p53-RV. K562 cells were infected with the p53-RV or NCV for 4 hours as described in Example II. The viral supernatant was removed and the cells were injected immediately into nude mice as described in Example III.

Tumorigenicity in Nude Mice of K562 Cells Following a Short-term Infection with p53-RV To further assess the tumor suppressive activity of the wild type p53 gene in K562 cells, and to determine whether a short-term infection protocol would be feasible for potential therapy of leukemias and lymphomas, K562 CML cells were co-incubated with p53-RV for four hours before testing for the malignant phenotype as determined by subcutaneous tumor formation in nude mice. Following a short-term infection by the p53-RV or the NCV, K562 cells were injected bilaterally into nude mice. In three separate experiments, substantial suppression of tumor formation on the flank injected with K562 exposed to the p53-RV was observed (FIG. 2).

EXAMPLE V

Growth Suppressive Activity of p53-RV on other Human Tumor Cell Types

Figure 3A:
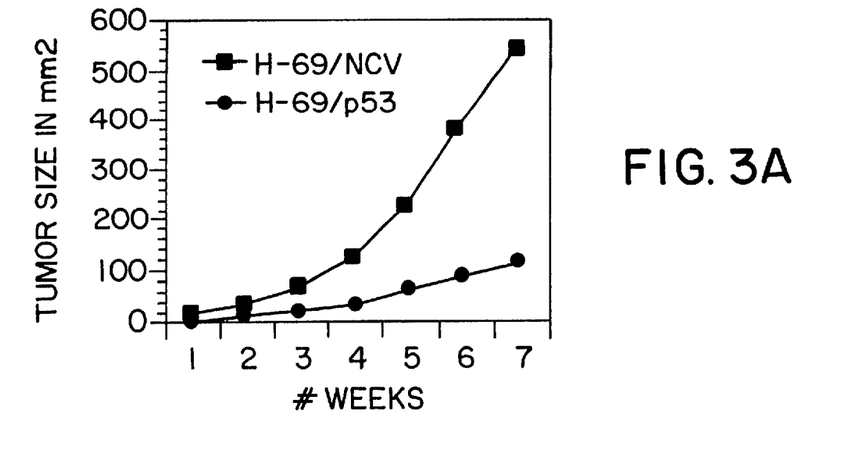
FIG. 3 shows delayed tumor formation in nude mice induced by three human cell lines following short-term infections with the p53-RV. The three human cells lines, H69 (human small-cell lung carcinoma), H128 (human small-cell lung carcinoma) and HTB9 (human bladder carcinoma), were obtained from the American Type Culture Collection (ATCC), (Rockville, Md.). The short-term infections using either p53-RV or NCV were performed as described in Examples II and III.
Figure 3B:
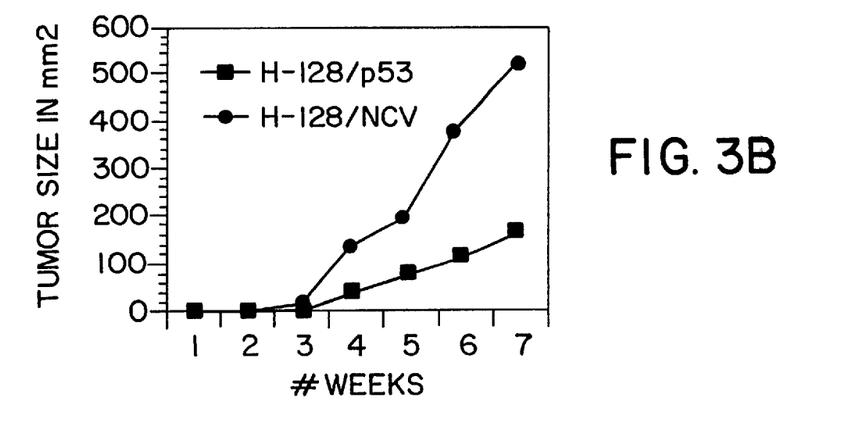
Figure 3C:
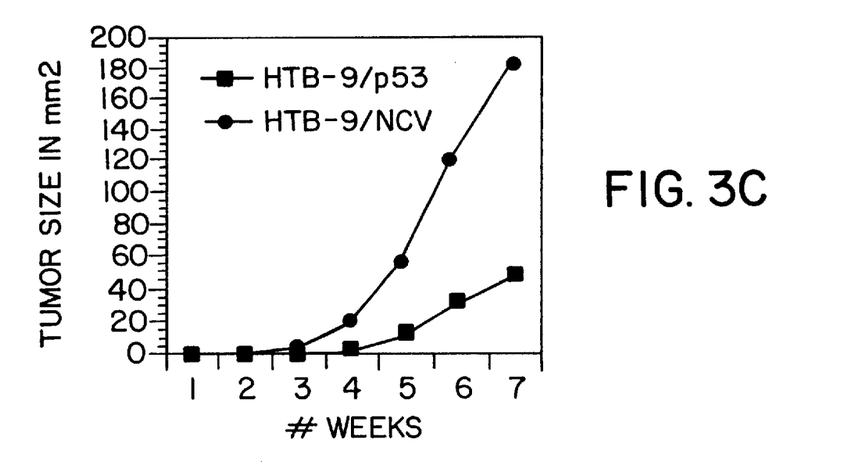
Figure 4A:
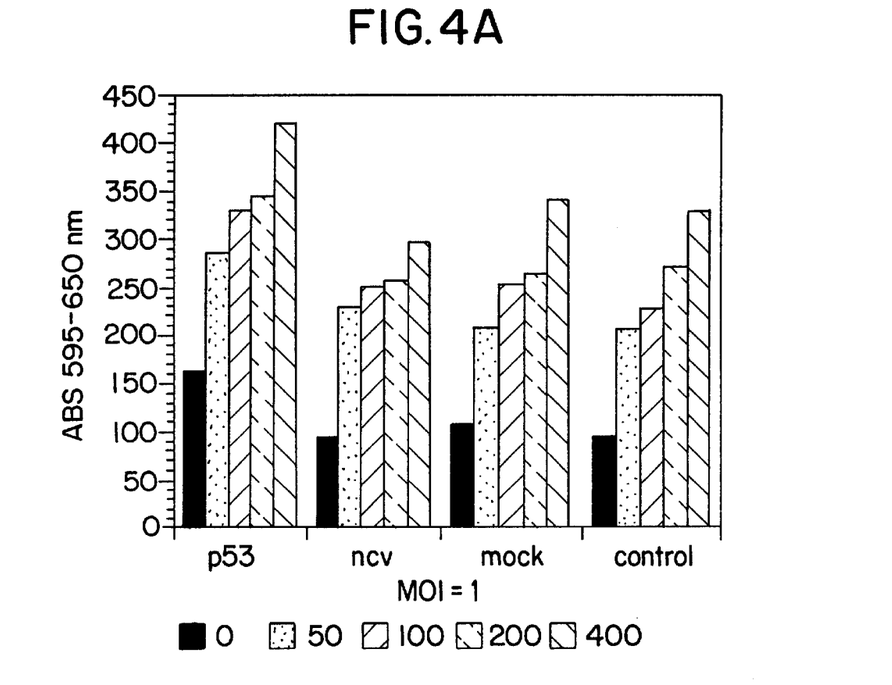
FIG. 4 shows lack of toxicity of the p53-RV viral supernatant on normal murine bone marrow cells at a high multiplicity. Normal mouse bone marrow cells were obtained from the femurs of Balb/c mice. The cells were isolated by ficoll-hypaque gradient, and infected with the p53-RV or NCV at MOI=1(A) or MOI=10(B) for 4 hours. At the end of infection, the viral supernatant was removed and the cells were seeded in 96-well plates at the density of $5 \times 10^4$ cells per well containing urine GM-CSF ranging from 0 to 400 units/ml. The cells were incubated for 3 days and the number of viable cells were determined by the MTT assay as described by Mossman, T., *J. Immunol. Methods*, 65:55–63 (1983).
Figure 4B:
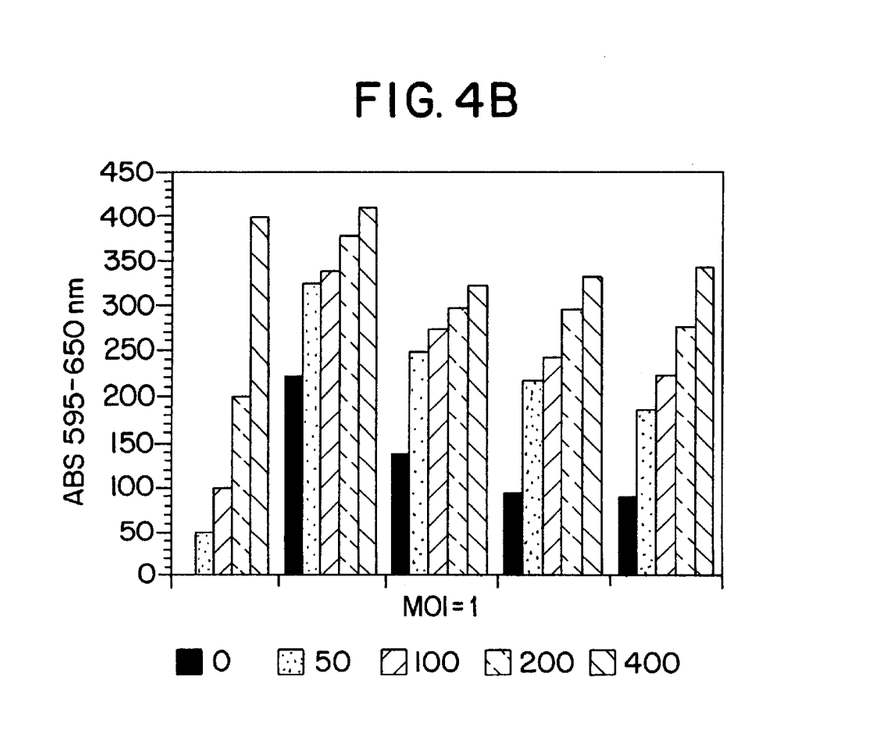

While the major target for clinical trials consists of leukemia and lymphoma patients, other cancer patients are currently under consideration for clinical trials involving marrow reconstitution (Miller, C. W. et al., *Can. Res.*, 52:1695–8 (1992); Takahashi, T. et al., *Oncogene*, 6:1775–8 (1991); Takahashi, T. et al., *Science*, 491–4 (1989)). FIG. 3 demonstrates that short-term infections of two small-cell lung carcinoma cell lines (H69 in FIG. 3A; H128 in FIG. 3B) lead to substantial inhibition of tumor growth in nude mice. In addition, a similar experiment was performed with a human transitional cell (bladder) carcinoma cell line (HTB-9 in FIG. 3C). In contrast, tumor cells infected with NCV grow rapidly in this tumor model (FIGS. 3A–C).

EXAMPLE VI

Preliminary in vitro Toxicity Studies

A critical issue for clinical application of the p53-RV has to do with whether introduction of the p53 coding sequence under control of a murine retroviral LTR may inhibit proliferation of normal bone marrow cells. Preliminary studies suggest that such inhibition is not an issue in this system. To determine toxicity of the p53-RV, it was investigated whether exposure of normal bone marrow cells to p53-RV under conditions similar to those employed for a short-term infection of K562 leukemic cells would have an effect on the response of normal bone marrow cells to GM-CSF. A three-day proliferation assay and a methylcellulose colony forming assay using either murine or human normal bone marrow cells were employed to ascertain such response. Exposure of murine bone marrow cells at either a MOI of 1.0 or 10.0 has no effect on their proliferation in response to GM-CSF. In addition, when either human (Table 3) or murine (data not shown) bone marrow cells were tested in a GM-CSF dependent colony forming assay, no effect on normal marrow progenitor colony forming units following exposure to the p53-RV as compared to NCV or mock infected controls was observed.

Normal human bone marrow cells were isolated by ficoll-hypaque gradient. These cells were incubated with the p53-RV, NCV, or growth media in the presence of 4 $\mu$g/ml polybrene for 4 hours. At the end of incubation, the cells were pelleted, and $1 \times 10^6$ cells per well were plated in 6-well plates containing 0.8% methylcellulose. Colonies larger than 50 cells per colony were scored 14 days later.

TABLE 5

| | COLONY NUMBER | | |
|---|---|---|---|
| | | rHuGMCSF | |
| Infection | None | 0.02 ng/ml | 0.04 ng/ml |
| Control | 1 | 18 | 21 |
| p53-RV (0.1) | 0 | 16 | 28 |
| NCV (0.1) | 0 | 11 | 18 |
| MOCK (0.1) | 2 | 12 | 17 |
| p53-RV (1.0) | 2 | 15 | 23 |
| NCV (1.0) | 4 | 9 | 18 |
| MOCK (1.00) | 0 | 25 | 18 |

EXAMPLE VII

Negative Purging of Small Cell Lung Cancer Cells (H69) from a Preparation of Human Bone Marrow Increasing quantities of small-cell lung cancer cell line H69 were added to human bone marrow cells. These cells were subjected to 3 two hour cycles of infection with p53-RV at a M.O.I. of 3. After infection the cells were pelleted and plated in methylcellulose. Colony formation is shown in Table 6. Suppression of tumor cell colony formation is evidenced in the p53-RV treated cultures, but is absent in the mock infected cultures. There is no evidence of suppression of bone marrow colony formation units in either case.

TABLE 6

Negative Purging of Small Cell Lung Cancer Cells (H69)
From a Preparation of Human Bone Marrow

| Colonies | 0 | 0.1 | 1.0 | 10.0 H69/HBMC % |
|---|---|---|---|---|
| A. Mock | | | | |
| H69 | 0 | 53 | 100 | 475 |
| HMBC + Growth Factors | 199 | 219 | 235 | 266 |
| B. P53-RV | | | | |
| H69 | 0 | 1 | 11 | 181 |
| HMBC + Growth Factors | 165 | 223 | 182 | 273 |
| HBMC + Growth | 81 | 48 | 84 | 171 |

HBMC = normal human bone marrow cells
$5 \times 10^5$ HBMC per well
HBMC + growth factors = total colony counts including H69, CFU-e, BFU-E, CFU-GEMM, and CFU-GM
Hyg = Hygromycin, 100 ug/ml

EXAMPLE VIII

Mixing Experiment to Study "Bystander Effect"

Five $(5) \times 10^7$ K562 cells (obtained from the American Type Culture Collection (ATCC)) were infected overnight with p53RV at a MOI equals 1 in RPMI medium containing 4 ug/ml polybrene (Sigma). Twenty-five nude mice were divided into 5 groups, with 5 animals per group. Every mouse in group 1 was infected subcutaneously with $5 \times 10^6$ of p53RV infected cells. The ratio of infected to uninfected cells=1:0. Every mouse in group 2 was injected subcutaneously with a mixture of $2.5 \times 10^6$ infected cells and $2.5 \times 10^6$ uninfected cells. The ratio of infected to infected cells=1:1. Every mouse in group 3 was injected subcutaneously with a mixture of $1.5 \times 10^6$ infected cells and $3 \times 10^6$ uninfected cells. The ratio of infected to uninfected cells=1:2. Every mouse in group 4 was injected subcutaneously with a mixture of $0.45 \times 10^6$ infected and $4.5 \times 10^6$ uninfected cells (infected:uninfected=1:10). All the mice in group 5 were injected subcutaneously with $5 \times 10^6$ uninfected cells (infected:uninfected=0:1). Nude mice were observed for tumor growth and survival time. Results of the study are summarized below.

| Group | Ratio infected:uninfected | Tumor Formation | Survival Status[b] |
|---|---|---|---|
| 1 | 1:0 | – | Alive and healthy at 200 days |
| 2 | 1:1 | – | Alive and healthy at 200 days |
| 3 | 1:2 | – | Alive and healthy at 200 days |
| 4 | 1:10 | – | Alive and healthy at 200 days |

| Group | Ratio infected:uninfected | Tumor Formation | Survival Status[b] |
|---|---|---|---|
| 5 | 0:1 | +[a] | All died within 90 days |

[a]Measurable tumors developed by thirtieth day.
[b]Experiment was terminated on day 200, when all p53RV-selected animals were till alive and healthy.

This experiment shows that treatment with p53RV, even at a MOI of less than 1, inhibits tumor formation or "tumorigenicity" in nude mice.

EXAMPLE IX

Effect of Intraperitoneal Injection of p53RV in K562 Bearing SCID Mice

Fifty (50) SCID mice were each injected i.p. with $25 \times 10^6$ K562 cells (ATCC). Within 50 days post-injection, leukemia developed in the mice. The mice were then randomly separated into 3 groups and treated as outlined below:

Group 1: injected i.p. with RPMI media on day 50

Group 2: injected i.p. with 1 ml heat-inactivated p53RV (original titer=$2.6 \times 10^5$ virus/ml, titer below detection limit after inactivation) on day 50

Group 3: injected i.p. with 1 ml p53RV ($2.6 \times 10^5$ virus/ml) on day 50

Mice treated with p53RV survived over twice as long as mice treated with heat-inactivated virus or control mice. Thus, systemic treatment with the retroviral vector containing the tumor suppressor gene p53 reduced tumorigenicity in the mice and prolonged survival time.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

We claim:

1. A method for purging tumor cells from a population of hematopoietic progenitor cells ex vivo, the method comprising contacting, in the absence of selection for retroviral infection, a mixed population of hematopoietic progenitor cells and tumor cells deficient in expression of endogenous wild-type p53 protein with a recombinant replication-incompetent retrovirus containing a nucleic acid that encodes a tumor suppressor p53 gene product, wherein a tumor cell phenotype of the transduced tumor cells is inhibited by the tumor suppressor p53 gene product.

2. The method of claim 1, wherein the suppressed tumor phenotype results in death of the tumor cells.

3. The method of claim 1, wherein the tumor cell is a prostate cell, a thyroid cell, a breast cell, a colon cell, a lung cell, a sarcoma cell, a leukemic cell, or a lymphoma cell.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 7 amino acids
      (B) TYPE: amino acid
      (C) STRANDEDNESS: Not Relevant
      (D) TOPOLOGY: Not Relevant    (ii) MOLECULE TYPE: peptide    (xi) SEQUENCE DESCRIPTION: SEQ ID NO:1:

Ser His Arg Pro Gly Ser Arg
1               5

(2) INFORMATION FOR SEQ ID NO:2:

(i) SEQUENCE CHARACTERISTICS:
      (A) LENGTH: 428 amino acids
      (B) TYPE: amino acid
      (C) STRANDEDNESS: Not Relevant
      (D) TOPOLOGY: Not Relevant    (ii) MOLECULE TYPE: peptide    (xi) SEQUENCE DESCRIPTION: SEQ ID NO:2:

Leu Leu Gly Ser Gly Asp Thr Leu Arg Ser Gly Trp Glu Arg Ala Phe
1           5                 10              15

His Asp Gly Asp Thr Leu Pro Trp Ile Gly Ser Gln Thr Ala Phe Arg
           20                25              30

Val Thr Ala Met Glu Glu Pro Gln Ser Asp Pro Ser Val Glu Pro Pro
      35                40              45

Leu Ser Gln Glu Thr Phe Ser Asp Leu Trp Lys Leu Leu Pro Glu Asn
   50               55              60

Asn Val Leu Ser Pro Leu Pro Ser Gln Ala Met Asp Asp Leu Met Leu
65               70              75              80

Ser Pro Asp Asp Ile Glu Gln Trp Phe Thr Glu Asp Pro Gly Pro Asp
           85                90              95

```
Glu Ala Pro Arg Met Pro Glu Ala Ala Pro Pro Val Ala Pro Ala Pro
            100                 105                 110
Ala Ala Pro Thr Pro Ala Ala Pro Ala Pro Ala Pro Ser Trp Pro Leu
        115                 120                 125
Ser Ser Ser Val Pro Ser Gln Lys Thr Tyr Gln Gly Ser Tyr Gly Phe
        130                 135                 140
Arg Leu Gly Phe Leu His Ser Gly Thr Ala Lys Ser Val Thr Cys Thr
145                 150                 155                 160
Tyr Ser Pro Ala Leu Asn Lys Met Phe Cys Gln Leu Ala Lys Thr Cys
                165                 170                 175
Pro Val Gln Leu Trp Val Asp Ser Thr Pro Pro Gly Thr Arg Val
                180                 185                 190
Arg Ala Met Ala Ile Tyr Lys Gln Ser Gln His Met Thr Glu Val Val
        195                 200                 205
Arg Arg Cys Pro His His Glu Arg Cys Ser Asp Ser Asp Gly Leu Ala
        210                 215                 220
Pro Pro Gln His Leu Ile Arg Val Glu Gly Asn Leu Arg Val Glu Tyr
225                 230                 235                 240
Leu Asp Asp Arg Asn Thr Phe Arg His Ser Val Val Val Pro Tyr Glu
                245                 250                 255
Pro Pro Glu Val Gly Ser Asp Cys Thr Thr Ile His Tyr Asn Tyr Met
                260                 265                 270
Cys Asn Ser Ser Cys Met Gly Gly Met Asn Arg Arg Pro Ile Leu Thr
                275                 280                 285
Ile Ile Thr Leu Glu Asp Ser Ser Gly Asn Leu Leu Gly Arg Asn Ser
        290                 295                 300
Phe Glu Val Arg Val Cys Ala Cys Pro Gly Arg Asp Arg Arg Thr Glu
305                 310                 315                 320
Glu Glu Asn Leu Arg Lys Lys Gly Glu Pro His His Glu Leu Pro Pro
                325                 330                 335
Gly Ser Thr Lys Arg Ala Leu Pro Asn Asn Thr Ser Ser Ser Pro Gln
                340                 345                 350
Pro Lys Lys Lys Pro Leu Asp Gly Glu Tyr Phe Thr Leu Gln Ile Arg
        355                 360                 365
Gly Arg Glu Arg Phe Glu Met Phe Arg Glu Leu Asn Glu Ala Leu Glu
    370                 375                 380
Leu Lys Asp Ala Gln Ala Gly Lys Glu Pro Gly Gly Ser Arg Ala His
385                 390                 395                 400
Ser Ser His Leu Lys Ser Lys Lys Gly Gln Ser Thr Ser Arg His Lys
                405                 410                 415
Lys Leu Met Phe Lys Thr Glu Gly Pro Asp Ser Asp
                420                 425
```